United States Patent [19]

Yabe et al.

[11] Patent Number: 4,576,650

[45] Date of Patent: * Mar. 18, 1986

[54] METHOD OF CLEANING ENDOSCOPE CHANNELS

[75] Inventors: Hisao Yabe; Hiroyuki Sasa; Yukio Nakajima; Fumiaki Ishii; Koji Takamura; Takeaki Nakamura, all of Tokyo, Japan

[73] Assignee: Olympus Optical Co., Ltd., Tokyo, Japan

[*] Notice: The portion of the term of this patent subsequent to Jun. 25, 2002 has been disclaimed.

[21] Appl. No.: 601,575

[22] Filed: Apr. 18, 1984

[30] Foreign Application Priority Data

Apr. 22, 1983 [JP] Japan ................................ 58-71204
Apr. 22, 1983 [JP] Japan ................................ 58-71205
Apr. 25, 1983 [JP] Japan ................................ 58-72522
May 2, 1983 [JP] Japan ................................ 58-77897

[51] Int. Cl.⁴ ............................ B08B 3/04; B08B 9/00
[52] U.S. Cl. ........................... 134/22.12; 134/22.18; 134/24; 134/34; 422/33
[58] Field of Search ................. 134/22.12, 22.18, 24, 134/166 C, 169 C, 171, 34; 128/6; 239/106, 112; 422/28, 33

[56] References Cited

U.S. PATENT DOCUMENTS

| 3,963,438 | 6/1976 | Banez. | |
|---|---|---|---|
| 4,064,886 | 12/1977 | Heckele | 134/171 X |
| 4,216,767 | 8/1980 | Aoshiro | 134/171 X |
| 4,278,101 | 7/1981 | Tanaka et al. | 134/171 X |
| 4,281,646 | 8/1981 | Kinoshita | 128/6 |
| 4,281,674 | 8/1981 | Tanaka et al. | 134/171 X |
| 4,288,882 | 9/1981 | Takeuchi | 134/199 X |
| 4,299,244 | 11/1981 | Hirai | 134/171 X |

Primary Examiner—Marc L. Caroff

[57] ABSTRACT

In a method of cleaning an endoscope, a stop is mounted on the open end of an air/liquid supply valve cylinder thereby closing the open end. A liquid tank is connected through a liquid supply tube to a first air supply port which opens to a connector of the endoscope and communicates with one end of an air supply channel. A connecting cap is attached to the connector so that a second air supply port communicating the air supply channel and a liquid supply port communicating with a liquid supply channel communicate with each other. An air supply pump is connected to the liquid tank. The pump is operated under this condition and supplies the liquid in the liquid tank to the first air supply port. The liquid supplied to the first air supply port is discharged from a nozzle communicating with the other ends of the air and liquid supply channels through these channels and the air/liquid supply valve cylinder, thereby cleaning the interior of these channels and the cylinder.

3 Claims, 9 Drawing Figures

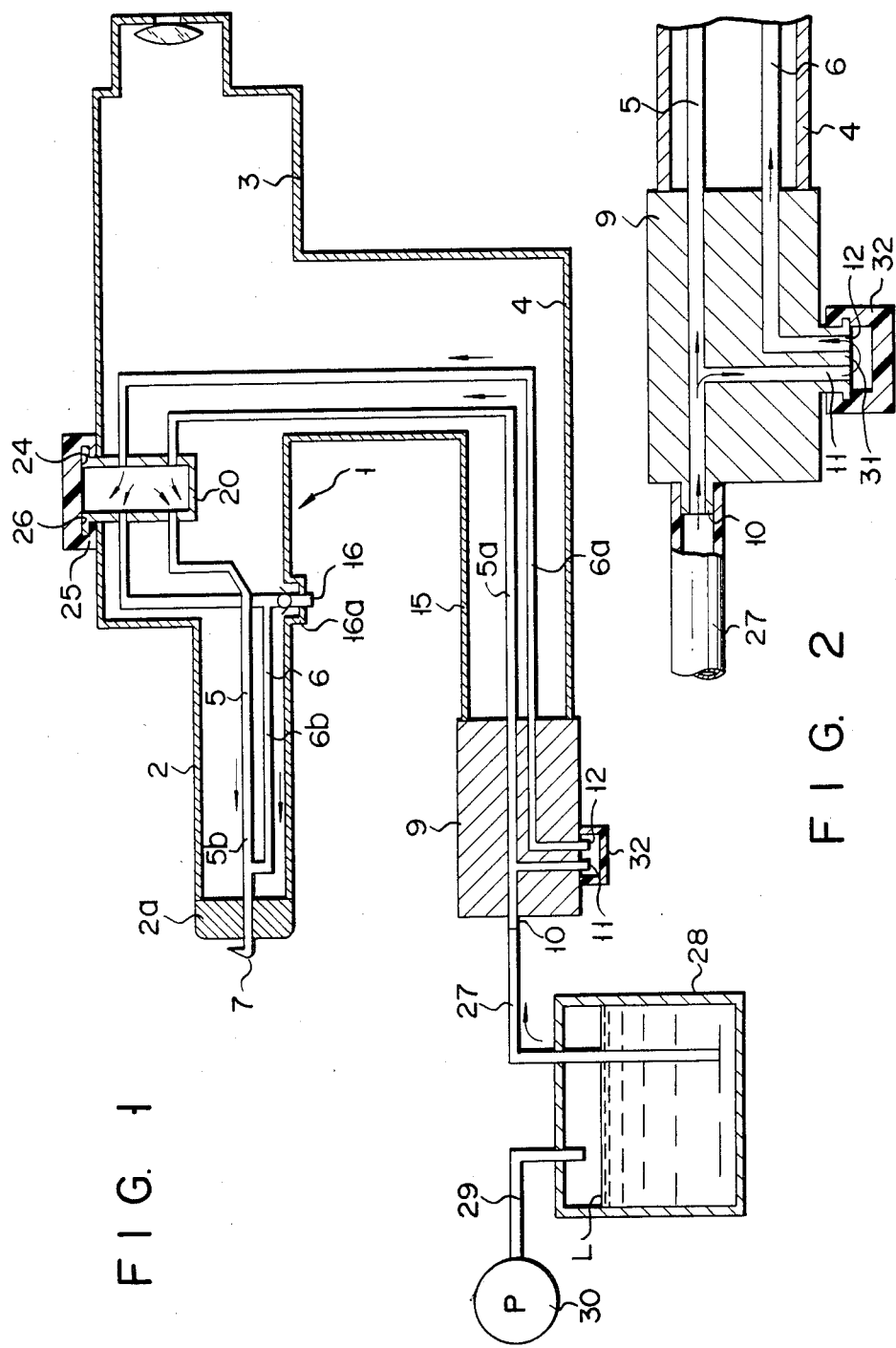

METHOD OF CLEANING ENDOSCOPE CHANNELS

BACKGROUND OF THE INVENTION

The present invention relates to a method of cleaning an endoscope.

An endoscope generally has various channels for supplying or drawing by suction air or liquids. Therefore, when a used endoscope is to be cleaned, not only the outer surface thereof but also the channel interiors must be cleaned. The word "cleaning" used herein includes the steps of water cleaning for removing contaminants in the channels, disinfection with a disinfectant after such water washing, and then water washing after disinfection. These cleaning steps are usually performed in the order named above. However, in a conventional method of cleaning the channel interiors, a cleaning solution injection tube must be inserted in the port of each channel, and the valve of each channel must be opened. This requires connection of the cleaning solution injection tube into each channel and a switching operation of the valve of each channel. Procedures for cleaning channels of an endoscope have therefore been complex. With the conventional system as described above, there is an important problem in that incomplete cleaning frequently occurs, especially of the small portions of the valve body of the valve or the portion of the cylinder which is covered with the valve body.

In view of this problem, the present applicant has previously proposed, in Japanese Patent Application No. 56-111940, a cleaning instrument for cleaning channels of an endoscope which is free from such a problem. According to this instrument, the cleaning solution is supplied through an air/liquid supply cylinder formed in a control section of an endoscope so as to allow simultaneous cleaning of the interiors of the channels and the inner surfaces of the cylinder. More specifically, a valve body inserted in the air/liquid supply cylinder is pulled out, and an adaptor is inserted in the open cylinder. A liquid supply tube connected to the adaptor is connected to a liquid supply pump. A liquid is supplied from the liquid supply pump to the cylinder. The liquid is then flowed from the cylinder to the nozzle at the distal end of the endoscope and to the air supply port and liquid supply port of the connector through the liquid supply channel and the air supply channel respectively, thereby cleaning these channels.

However, the various channels of an endoscope generally have different inner diameters. More specifically, those portions of the air supply channel and liquid supply channel which extend in the insertion section of the endoscope have a small diameter, and those portions of the channels which extend in the light guide cable have a large diameter. For this reason, when a liquid is supplied from the cylinder to the respective channels, the liquid flows to the channel or channel portion offering the least flow resistance, and a sufficient amount of cleaning solution cannot be flowed to a channel or channel portion offering a larger flow resistance. This results in a problem of incomplete cleaning of the endoscope.

SUMMARY OF THE INVENTION

Accordingly, the object of the present invention is to provide a method of cleaning an endoscope, which makes it possible to easily and completely clean the channels and valve cylinders of an endoscope.

According to an aspect of the invention there is provided a method of cleaning an endoscope, which comprises a first step of closing the open end of an air/liquid supply valve cylinder; and a second step of supplying liquid from the following three ports and sending the liquid through an air supply channel, a liquid supply channel and the air/liquid supply valve cylinder, thereby cleaning the interiors of these channels and the cylinder: (a) one end of the air supply channel; (b) one end of the liquid supply channel; (c) a sub-liquid port.

BRIEF DESCRIPTION OF THE DRAWINGS

FIG. 1 is a cross-sectional view of an endoscope, showing how to clean the channels of the endoscope by a first method according to the invention;

FIG. 2 is an enlarged sectional view of the connector of the endoscope shown in FIG. 1;

DETAILED DESCRIPTION OF THE PREFERRED EMBODIMENTS

Figure 3:
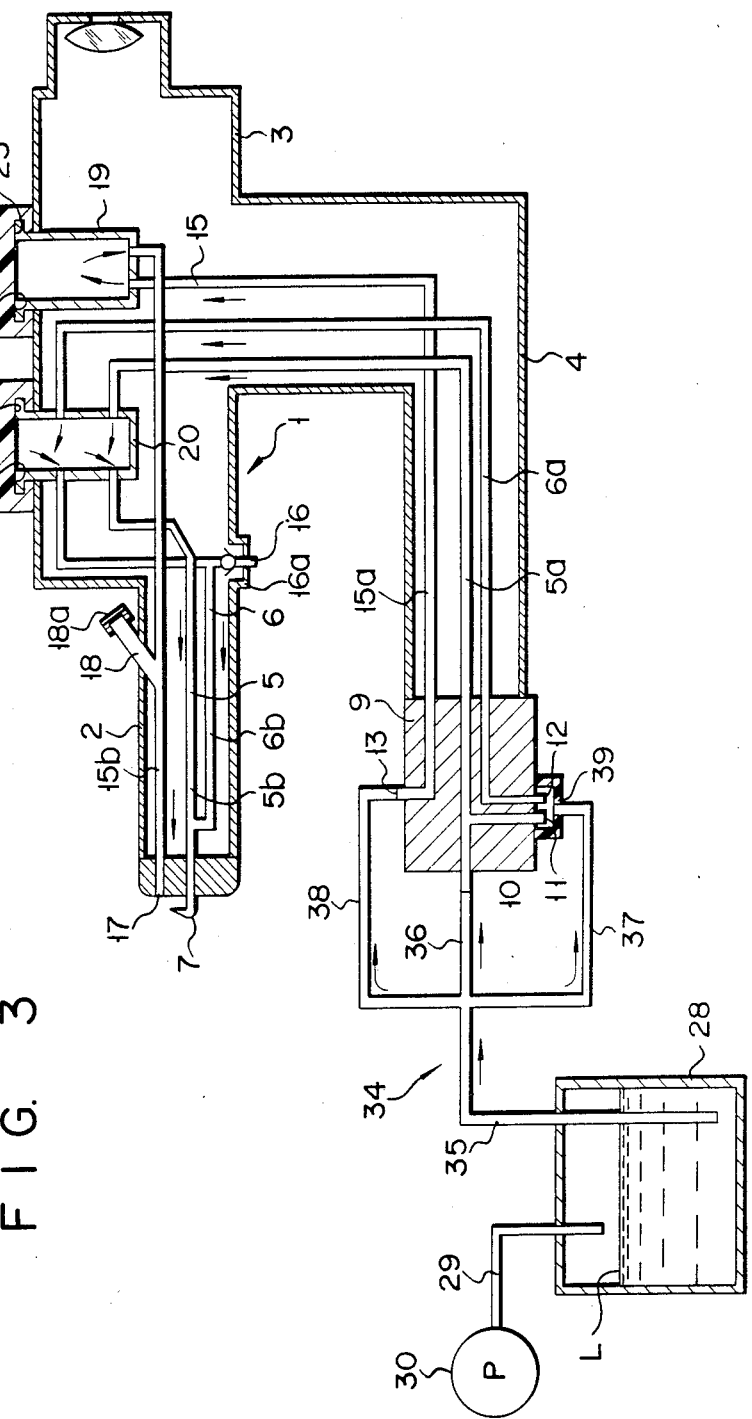
FIG. 3 is a cross-sectional view of another endoscope, showing how to clean the channels of the endoscope by a second method according to the invention.

A few preferred embodiments of the present invention will now be described with reference to the accompanying drawings.

FIG. 1 is a cross-sectional view of an endoscope 1. The endoscope 1 comprises a control section 3, an insertion section 2 extending from the control section 3 and a light guide cable 4 extending from the control section 3. Various channels (described later) are formed inside the endoscope 1. First, an air supply channel 5 and a liquid supply channel 6 are formed extending through the insertion section 2, the control section 3 and the light guide cable 4. The distal ends of the air supply channel 5 and the liquid supply channel 6 merge to be connected to an air/liquid supply nozzle 7 at the distal end 2a of the insertion section 2. The air/liquid supply nozzle 7 is arranged to face the outer surface of an observation window (not shown) so as to spray air or a liquid thereagainst. The light guide cable 4 has a connector 9 at the free end. The connector 9 has first and second air supply ports 10 and 11 both communicating with the air supply channel 5, and a liquid supply port 12 communicating with the liquid supply channel 6. When the connector 9 is connected to a light source device (not shown), the first air supply port 10 is connected to an air supply pump in the light source device. The second air supply port 11 and the liquid supply port 12 are connected to a liquid supply tank (not shown). A sub-liquid supply port 16 is formed in the control section 3. It communicates with the liquid supply channel 6 through a check valve 16a.

Meanwhile, an air/liquid supply cylinder or air/liquid supply valve cylinder 20 is inserted midway along both the air supply channel 5 and the liquid supply channel 6. The upper end of the valve cylinder 20 opens to the outside of the control section 3. The air/liquid supply valve cylinder 20 has a bottom and has a flange 24 formed integrally at its open edge. A stop 25 is attached to the valve cylinder 20 to close the open end. An engagement groove 26 engaging with the flange 24 is formed in the inner surface of the stop 25, so that the stop 25 may not be inadvertently removed, even if the internal pressure in the valve cylinder 24 is increased.

A piston (not shown) is generally inserted in the air/liquid supply valve cylinder 20. The piston serves to allow or block communication between upstream channel portions 5a and 6a and downstream channel portions 5b and 6b of the air supply channel 5 and the liquid supply channel 6, respectively. However, when the stop 25 is to be mounted on the cylinder 20, the piston is removed first.

One end of a liquid supply tube 27 is connected to the first air supply port 10. The other end portion of the liquid supply tube 27 is air-tightly inserted into a liquid tank 28 filled with liquid L, and the distal end of the tube 27 is submarged in the liquid L. One end of a pressurizing tube 29 is air-tightly connected to the liquid tank 28. One end of the pressurizing tube 29 opens to the upper space within the liquid tank 28 and the other end thereof is connected to an air supply pump 30. When the pump 30 is operated and raises the internal pressure of the liquid tank 28, the liquid L is supplied from the liquid supply tube 27. As shown in FIG. 2, the second air supply port 11 and liquid supply port 12 open to a mouthpiece 31 of the connector 9. A connecting cap 32 made of resilient material such as rubber is mounted on the mouthpiece 31. The second air supply port 11 and liquid supply port 12 communicate through the internal space of the connecting cap.

The method of cleaning the endoscope 1 will now be described. First, as shown in FIG. 1, the stop 25 is attached to the air/liquid supply valve cylinder 20. At the same time, the liquid supply tube 27 is connected to the first air supply port 10 of the connector 9, while the connecting cap 32 is mounted on the mouthpiece 31 so that the second air supply port 11 and liquid supply port 12 communicate with each other. When the air supply pump 30 is operated under this condition, the liquid tank is pressurized by the air from the air supply pump. The liquid L is therefore supplied from the liquid supply tube 27 to the upstream channel portion 5a of the air supply channel 5. Part of the liquid which has flowed into the air supply channel 5 enters the upstream channel portion 6a of the liquid supply channel 6 through the internal space in the connecting cap 32. The liquid L further flows from the upstream channel portions 5a and 6a into the air/liquid supply valve cylinder 20 to wash the interior of the cylinder. Then, it flows from the nozzle 7 through the downstream channel portions 5b and 6b of the air supply channel 5 and the liquid supply channel 6.

With the flow of the liquid L described above, the respective channels 5 and 6 can be cleaned along their entire length, and, at the same time, the interior of the air/liquid supply valve cylinder 20 can be cleaned. Since the liquid L flows in such a direction as to flow outward from the nozzle 7, contaminants can be completely removed from the nozzle.

In the above description, the liquid is water or disinfectant. In general, disinfection is performed with a disinfectant. However, the term "cleaning" used herein includes both washing with water and disinfection or sterilization.

According to the first embodiment, as has been described above, when the air/liquid supply valve cylinder is closed and the air and liquid supply ports of the connector are connected to each other, the liquid is supplied from the air supply port and discharged from the nozzle of the insertion section. Therefore, as the liquid flows as discribed above, the air supply channel and liquid supply channel can be completely cleaned along their entire length, and the interior of the valve cylinder can be cleaned at the same time. Since the liquid is compulsorily supplied from the ports of the connector to the channels and discharged from the distal end of the insertion section, the channels can be completely cleaned along their entire length even if the respective channels have different inner diameters. Moreover, the liquid flows in such a direction as to flow outward from the nozzle, so that contaminants attached to the nozzle can be exhausted. The method also provides an excellent operability since no special operation is required for supplying the liquid to the endoscope.

Although the first embodiment is used in convination with the endoscope 1 which does not have a suction valve cylinder on a suction channel, the method of the present invention can be also applied to an endoscope which has a suction channel and a suction valve cylinder.

Figure 4:
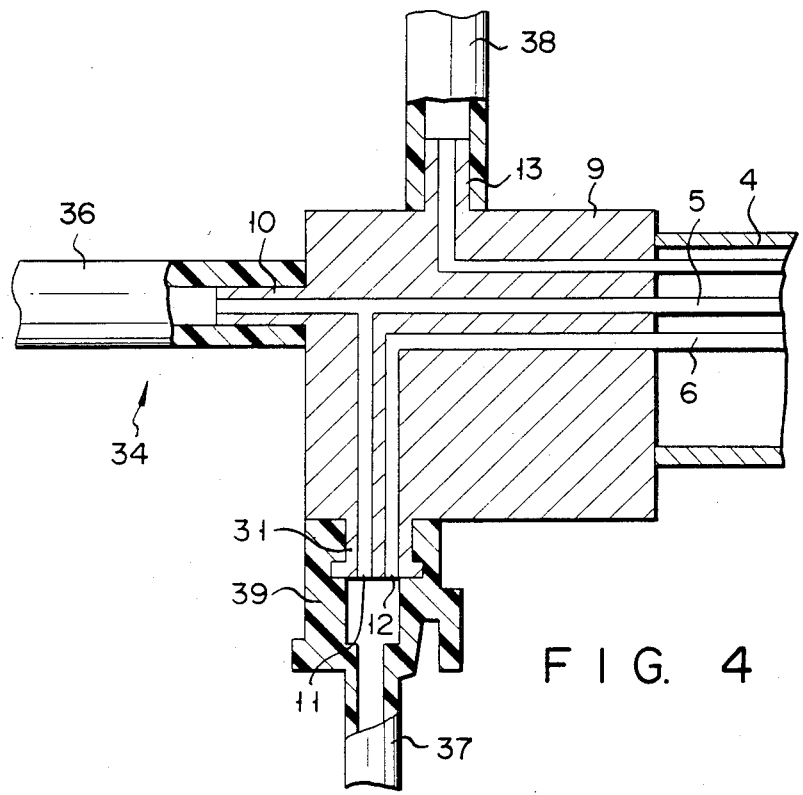
FIG. 4 is an enlarged sectional view of the connector of the endoscope shown in FIG. 3.

FIGS. 3 and 4 show a second embodiment applied to the cleaning of an endoscope 1 which has a suction channel 15 and a suction valve cylinder 19. Of the members forming this embodiment, only those which are different from the members constituting the first embodiment will be described in detail. In FIGS. 3 and 4, the same numerals are used to designate like or the same members as those of the first embodiment.

In the second embodiment, the suction channel 15 extends along the entire length of an insertion section 2, a control section 3 and a light guide cable 4. That end portion of the suction channel 15 which is at the side of the insertion section 2 serves as an instrument insertion channel 15b. The distal end of the instrument insertion channel 15a communicates with a suction opening 17 opening to the distal end of the insertion section 2. The proximal end of the instrument insertion channel 15b opens externally at the control section 3 to form a forceps port 18. The forceps port 18 is closed with a detachable stop 18a. The instrument insertion channel 15b is connected to the proximal end of the remaining portion of the suction channel 15 through the suction valve cylinder 19. The cylinder 19 is arranged next to an air/liquid supply valve cylinder 20 at a side surface of the control section 3. The upper end of the suction valve cylinder 19 opens to the outside of the control section.

The suction valve cylinder 19 has a bottom and has a flange 23 formed integrally therewith at its open edge or upper edge. A step 22 is attached to the valve cylinder 19 to close the open end. An engaging groove 33 is formed in the inner surface of the stop 22. The flange 23 engages this groove 33 so that the stop may not be removed, even if the internal pressure of the suction valve cylinder 19 increases. Generally, a piston (not shown) is inserted in the suction valve cylinder 19 to allow or block communication between the upstream channel portion 15a and downstream channel portion 15b. However, to mount the stop 22 on the cylinder 19, the piston is removed first. Meanwhile, the other end of the suction channel 15 communicates with a suction port 13 formed in a connector 9.

As shown in FIG. 4, a liquid supply tube 34 is connected to an air supply ports 10, 11, a liquid supply port 12 and the suction port 13 of the connector 9. The liquid supply tube 34 has a main channel portion 35 and first to third connecting channel portions 36, 37 and 38 which diverge from one end of the main channel portion. The first connecting channel portion 36 is connected to the first air supply port 10. The second connecting channel portion 37 has at its distal end a connecting mouthpiece 39 which is connected to a mouthpiece 31 of the connector 9. The second air supply port 11 and the liquid supply port 12 open to the mouthpiece 31. The third connecting channel portion 38 is connected to the suction port 13.

The other end portion of the main channel portion 35 of the liquid supply tube 34 is air-tightly inserted in a liquid tank 28 filled with liquid L. The distal end of the tube is submarged in the liquid L. One end of a pressurizing tube 29 is air-tightly connected to the liquid tank 28 and opens to the upper space within the tank 28. The other end of the pressurizing tube 29 is connected to an air pump 30.

The method of cleaning the endoscope 1 according to the second embodiment will now be described. First, as shown in FIG. 3, the stops 25 and 22 are attached to the valve cylinder 20 and 19, respectively. The first to third connecting channel portions 36, 37 and 38 of the liquid supply tube 34 are connected to the ports 10, 11, 12 and 13, respectively. When the air pump 30 is operated under this condition, the liquid tank 28 is pressurized by the air from the air supply pump 30 and the liquid L is supplied from the first, second and third connecting channel portions 36, 37 and 38 of the liquid supply tube 34 to the upstream channel portions 5a, 6a and 15a of the air supply channel 5, the liquid supply channel 6 and the suction channel 15. The liquid which has flowed into the upstream channel portions 5a and 6a of the air supply channel 5 and the liquid supply channel 6 flows into the air/liquid supply valve cylinder 20 to wash the interior of the cylinder 20, and then flows from the nozzle 7 through the downstream channel portions 5b and 6b of the air and liquid supply channels. The liquid L flows from the upstream channel portion 15a of the suction channel 15 into the suction valve cylinder 19 to wash the interior of the cylinder 19, and then flows out of the suction opening 17 through the downstream channel potion 15b.

As the liquid L flows as described above, the respective channels 5, 6 and 15 and the valve cylinders 19 and 20 can be as easily and completely cleaned as in the first embodiment.

Figure 5:
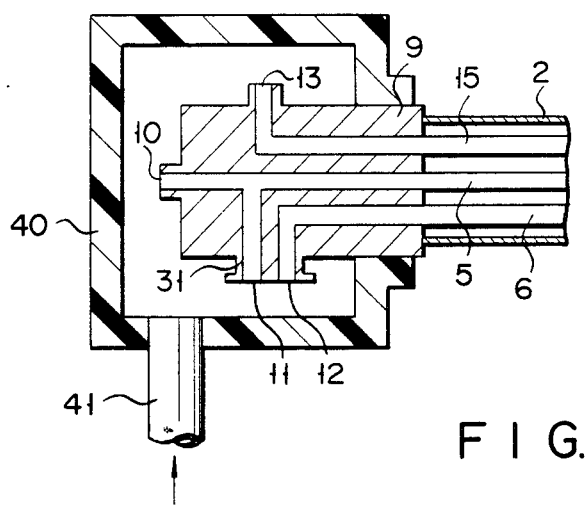
FIG. 5 is an enlarged sectional view of the connector shown in FIG. 3 and a cap covering the connector.

In the second embodiment, if a small hole is formed in the stop 18 mounted at the forceps port 18 to allow outward flow of the liquid L through this small hole in a small amount, the forceps port 18 can be reliably cleaned. Also, instead of using the liquid supply tube 34, a cap 40 made of resilient material such as rubber can be attached to the connector 9 to cover it and the liquid tank 28 can be connected to the cap through a single liquid supply tube 41, as shown in FIG. 5.

Figure 6:
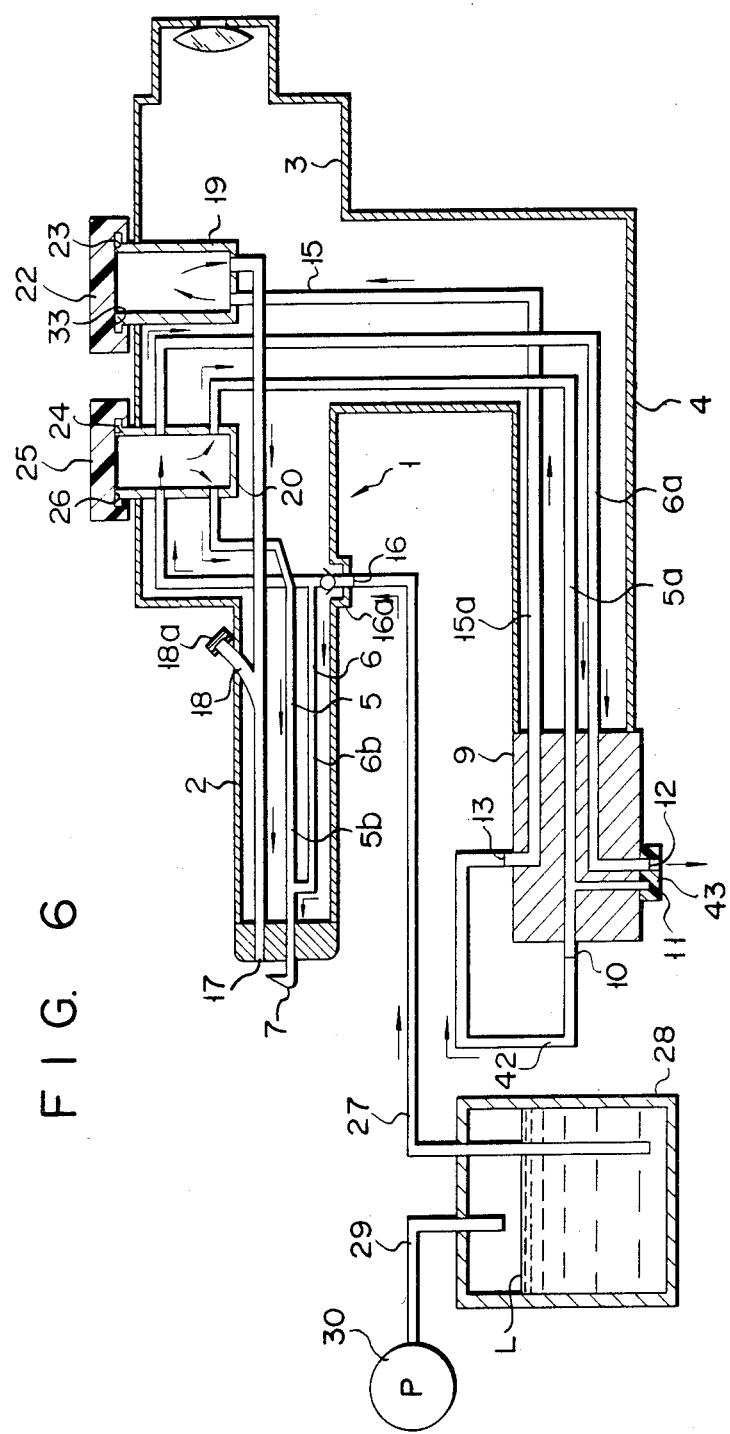
FIG. 6 is a cross-sectional view of the another endoscope, showing how to clean the channels by a third method according to the invention.
Figure 7:
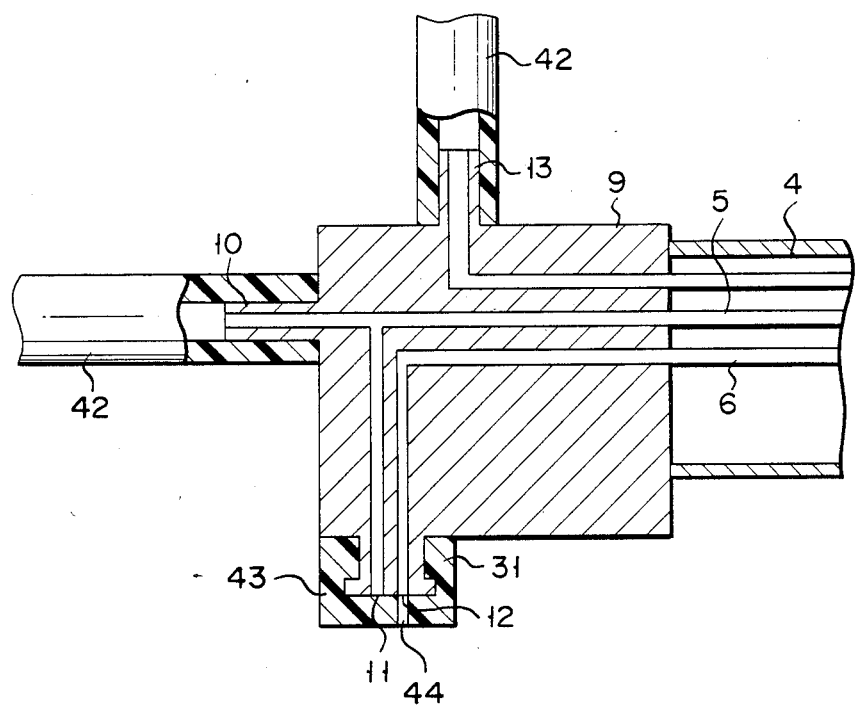
FIG. 7 is an enlarged sectional view of the connector of the endoscope shown in FIG. 3 and a connecting tube.

In the second embodiment, the liquid L is supplied from the ports 10, 11, 12 and 13, however the liquid can be supplied from a sub-liquid supply port 16 of the endoscope 1, as shown in FIGS. 6 and 7. In this embodiment, one end of a liquid supply tube 27 is connected to the sub-liquid supply port 16. The other end portion of the tube 27 is air-tightly inserted into a liquid tank 28 filled with liquid L. The distal end of the tube 27 is submarged in the liquid. One end of a pressurizing tube 29 is connected to the liquid tank 28 and opens to the upper space in the tank. The other end of the tube 29 is connected to the air supply pump 30.

The first air supply port 10 and suction port 13 are connected by a connecting tube 42. A cap 43 is attached to the mouthpiece 31 to which the second supply air port 11 and liquid supply port 12 open. The cap 43 has a through hole 44 which connects the liquid supply port 12 to the outside. The second air supply port 11 is closed by the cap 43.

In ths third embodiment, when the air supply pump 30 is operated and the liquid L in the tank 28 is pressurized by the air from the pump, the liquid L presses the check valve 16a to open it and flows into the downstream channel portion 6b of the liquid supply channel 6 from the sub-liquid supply port 16. Part of the liquid L which has flowed into the downstream channel portion 6b is discharged from the nozzle 7, and the remainder flows into the air/liquid supply valve cylinder 20. The liquid L which has supplied to the cylinder 20 flows out of the nozzle 7 through the downstream channel portion 5b of the air supply channel 5. It flows into the upstream channel portions 5a and 6b of the air supply channel and the liquid supply channel 6. The liquid L flows from the upstream channel portion 6a outward through the liquid supply port 12 and the through hole 44. The liquid L which has flowed into the upstream channel portion 5a of the air supply channel 5 flows into the upstream channel portion 15a of the suction channel 15 through the connecting tube 42 and the suction port 13, and is then exhausted from the suction opening through the downstream channel portion 15b of the suction channel via the suction valve cylinder 19.

According to the third embodiment described above, all the channels 5, 6 and 15 and both valve cylinders 19 and 20 can be simultaneously cleaned, as in the second embodiment.

In this third embodiment, if a small hole is formed in the cap 43 mounted on the mouthpiece 31 to allow outward flow of the liquid L, the inner peripheral surface of the second air supply port 11 can be reliably cleaned.

The present invention can also be applied to an endoscope which has a gas supply valve and a gas supply channel.

Figure 8:
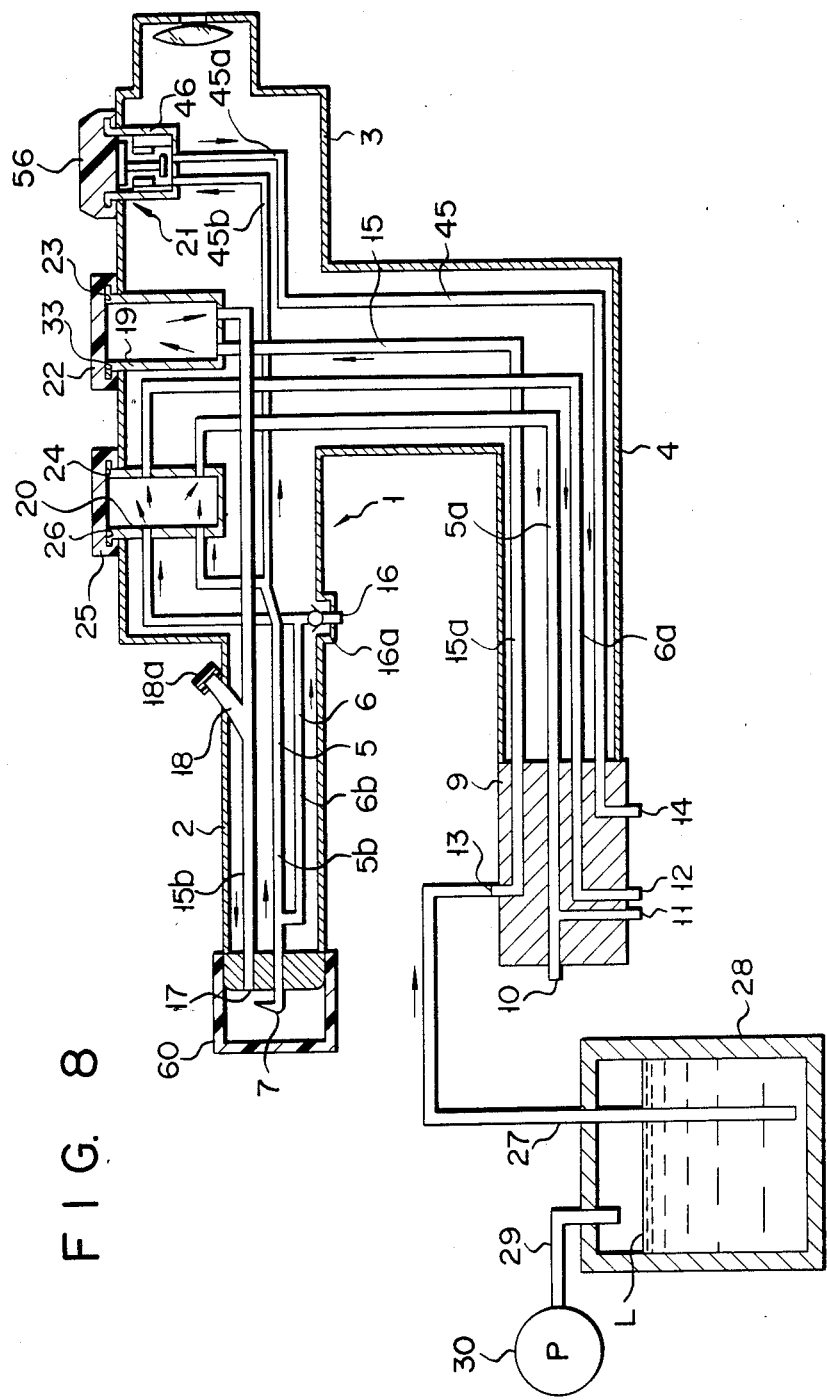
FIG. 8 is a cross-sectional view of another endoscope, showing how to clean the channels by a fourth method according to the invention.
Figure 9:
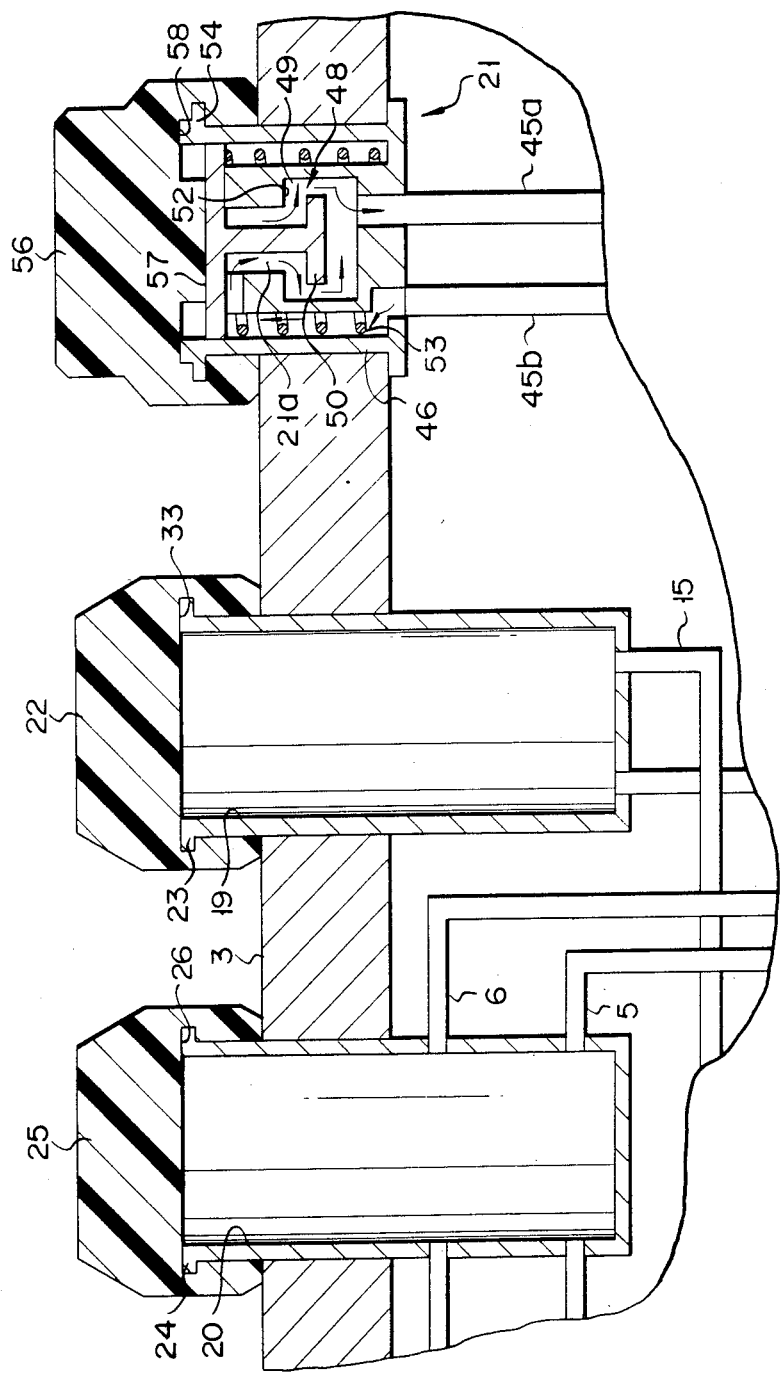
FIG. 9 is an enlarged sectional view of the control section of the endoscope shown in FIG. 8.

FIGS. 8 and 9 show a fourth embodiment applied to an endoscope which has a gas supply valve and a gas supply channel. Of the members forming this embodiment, only those which are different from the members constituting the second embodiment will be described.

In the fourth embodiment, a gas supply valve 21 is arranged in a control section 3 of an endoscope 1 and next to a suction valve 19. A gas supply channel 45 is connected to the gas supply valve 21. One end of the gas supply channel 45 is connected to an air supply channel 5 at a position between an air/liquid supply valve cylinder 20 and a nozzle 7. The other end of the gas supply channel 45 communicates with a gas supply port 14 which opens to a connector 9 mounted on the distal end of a light guide cable 4. The gas supply valve 21 has the construction shown in FIG. 9. It includes a cylinder 46 and a valve mechanism 48 mounted therein. A valve chamber 49 is formed concentrically in the cylinder 46. A valve body 50 which may be brought into contact with a valve seat 52 is arranged inside the valve chamber 49. The valve body 50 is normally biased by a coil spring 53 to be in contact with the valve seat 52, that is, biased in the valve closing direction. Thus, the valve body 50 normally provides a seal in a path 21a connecting an upstream channel portion 45a and a downstream channel portion 45b of the gas supply channel 45. A flange 54 is formed integrally with the open end of the cylinder 46. A stop 56 is mounted in the cylinder 46 of the gas supply valve 21 to close its open end. A projection 57 projects downward from the center of the stop 56. When the stop 56 is mounted on the cylinder 46, the projection 57 presses the valve body 50 against the biasing force of the coil spring 53, so that the valve body 50 is separated from the valve seat 52 to open the path 21a. An engagement groove 58 is formed in the stop 56 for engagement with the flange 54.

A detachable cap 60 is air-tightly attached to the distal end of an insertion section 2 of the endoscope 1. A nozzle 7 and a suction opening 17 which are located at the distal end of the insertion section 2 communicate through the internal space in the cap 60. One end of a liquid supply tube 27 is connected to a suction port 13 open to the connector 9. The other end portion of the liquid supply tube 27 is air-tightly inserted into a liquid tank 28 filled with liquid L and the distal end thereof is submerged in the liquid. One end of a pressurizing tube 29 is air-tightly connected to the liquid tank 28 and opens to the upper space in the liquid tank. The other end of the pressurizing tube 29 is connected an air supply pump 30.

The method of cleaning the endoscope 1 according to the fourth embodiment will now be described. First, as shown in FIG. 8, the stops 22, 25, 56 and 18a are mounted on the cylinders 19, 20 and 21 and the forceps port 18, respectively. At the same time, the air supply tube 27 is connected to the suction port 13, while the cap 60 is attached to the distal end of the insertion section 2. When the air supply pump 30 is operated under this condition, the liquid L in the liquid tank 28 is supplied therefrom along the liquid supply tube 27 and into the upstream channel portion 15a of the suction channel 15 through the suction port 13. The liquid L which has flowed into the upstream channel portion 15a flows into the downstream channel portion 15b of the suction channel 15 through the suction valve cylinder 19. It is discharged from the suction opening 17 into the cap 60. At this time the forceps port 18 is closed by the stop 18a. Hence, the liquid does not flow out from the forceps port. The liquid L which has flowed into the cap 60 then flows into the air/liquid supply valve cylinder 20 through the downstream channel portions 5b and 6b of the air supply channel 5 and the liquid supply channel 6 via the nozzle 7. The liquid L in the air/liquid supply valve cylinder 20 flows into the upstream channel portions 5b and 6b of the channels 5 and 6. It flows out of the first and second air supply ports 10 and 11 and the liquid supply port 12. Part of the liquid L, which has flowed into the downstream channel portion 5b of the air supply channel 5, flows into the gas supply valve cylinder 46 through the downstream channel portion 45b of the gas supply channel 45. The liquid L which has been supplied to the gas supply valve cylinder 46 flows into the upstream channel portion 45a of the gas supply channel 45 through the inside of the cylinder 46 as indicated by the arrows in FIG. 9 and then flows out from the gas supply port 14.

With the flow of the liquid L described above, all the channels and cylinders of the endoscope 1 can be simultaneously cleaned, as in the above embodiments.

In the fourth embodiment, the liquid L is supplied from the suction port 13 to the endoscope 1, however, the liquid can be supplied from one of the other ports 10, 11, 12 and 14.

The present invention is not limited to the above embodiments. For example, the present invention can also be similarly applied to an endoscope in which an air supply channel and a liquid supply channel communicate with separate nozzles at a distal end of an insertion section. Moreover, the means for supplying liquid is not limited to the air supply pump but can be a piston-type syringe.

What is claimed is:

1. A method of cleaning an endoscope; said endoscope including a control section, an insertion section extending from the control section and having a nozzle at a distal end thereof, a light guide cable extending from the control section and having a connector at a distal end thereof, an air supply channel extending in the endoscope and having one end communicating with the nozzle and another end opening into the connector, a liquid supply channel extending in the endoscope and having one end communicating with the nozzle and another end opening into the connector, a suction channel extending in the endoscope and having one end opening to the distal end of the insertion section and another end opening into the connector, an air/liquid supply valve cylinder arranged in the control section to communicate with the air supply channel and liquid supply channel and having one end opening to the outside of the control section, a suction valve cylinder arranged in the control section to communicate with the suction channel and having one end opening to the outside of the control section, and a sub-liquid supply port communicating with the liquid supply channel; said method comprising the steps of:

closing said open ends of the air/liquid supply valve cylinder and the suction valve cylinder;

connecting said other ends of the air supply channel and the suction channel to each other through connecting means; and supplying liquid to the sub-liquid supply port and discharging the liquid from the nozzle, said other end of the liquid supply channel and said one end of the suction channel through the three channels, the valve cylinders and the connecting means, thereby cleaning the interior of these channels and the valve cylinders with the liquid.

2. A method of cleaning an endoscope, said endoscope including a control section, an insertion section extending from the control section and having a nozzle at a distal end thereof, a light guide cable extending from the control section and having a connector at a distal end thereof, an air supply channel extending in the endoscope and having one end communicating with the nozzle and another end opening into the connector, a liquid supply channel extending in the endoscope and having one end communicating with the nozzle and another end opening into the connector, a suction channel extending in the endoscope and having one end opening into the distal end of the insertion section and another end opening into the connector, an air/liquid supply valve cylinder arranged in the control section to communicate with the air supply channel and liquid supply channel and having one end opening to the outside of the control section, a gas supply channel extending in the endoscope and having one end communicating with the air supply channel at a position between the nozzle and the air/liquid supply valve cylinder and another end opening into the connector, a suction valve cylinder arranged in the control section to communicate with the suction channel and having one end opening to the outside of the control section, a gas supply valve cylinder arranged in the control section to communicate with the gas supply channel and having one end opening to the outside of the control section, and a sub-liquid supply port communicating with the liquid supply channel; said method comprising the steps of:

closing said open ends of the air/liquid supply valve cylinder, the suction valve cylinder and the gas supply valve cylinder;

mounting communicating means on the distal end of the insertion section so that liquid is confined to flow between the nozzle and said one end of the suction channel; and supplying liquid to at least one of the following five ports and sending the liquid through the four channels, the three valve cylinders and the communicating means, thereby cleaning the interior of these channels and the valve cylinders with the liquid:
(a) the other end of the air supply channel,
(b) the other end of the liquid supply channel,
(c) the sub-liquid supply port,
(d) the other end of the suction channel,
(e) the other end of the gas supply channel.

3. A method according to claim 2, wherein said second step includes: supplying liquid to the other end of the suction channel and discharging the liquid from the other ends of the air supply channel, liquid supply channel and gas supply channel through the four channels, the three valve cylinders, and the communicating means.

* * * * *